US00PP25076P3

(12) United States Plant Patent
Zwetzig

(10) Patent No.: US PP25,076 P3
(45) Date of Patent: Nov. 18, 2014

(54) ***HIBISCUS* PLANT NAMED 'SNOWFLAME'**

(50) Latin Name: *Hibiscus moscheutos×H. coccineus*
Varietal Denomination: Snowflame

(75) Inventor: Gretchen Zwetzig, Lindsay, CA (US)

(73) Assignee: Gretchen Zwetzig/Flemings Flower Fields, Lindsay, CA (US)

( * ) Notice: Subject to any disclaimer, the term of this patent is extended or adjusted under 35 U.S.C. 154(b) by 119 days.

(21) Appl. No.: 12/932,387

(22) Filed: Feb. 24, 2011

(65) Prior Publication Data

US 2012/0222179 P1 Aug. 30, 2012

(51) Int. Cl.
*A01H 5/00* (2006.01)
*A01H 5/02* (2006.01)

(52) U.S. Cl.
CPC ..... *A01H 5/02* (2013.01)
USPC ..... Plt./257

(58) Field of Classification Search
CPC ..... A01H 5/02; A01H 5/00
USPC ..... Plt./257
See application file for complete search history.

(56) References Cited

PUBLICATIONS

Wilders. California Gardens: Time to plant fall veggies. North County Times, Sep. 4, 2009, 2 pp.*

* cited by examiner

*Primary Examiner* — June Hwu

(57) ABSTRACT

A new and distinct cultivar of winter hardy *Hibiscus* plant named 'Snowflame' is the result of a unique hybridization. This new and distinct cultivar is characterized primarily as to its novelty by its extreme cold hardiness to Zone 4, its large thick-textured, light red flowers with white reverse and its "Maple-shaped" leaves with a red-dish-green coloration, compactness of about 3 feet, its vigorous and uniform growth habit and its floriferous nature from midsummer until frost.

1 Drawing Sheet

*Hibiscus* plant named: 'Snowflame'.
Latin name: *Hibiscus moscheutos×H. coccineus.*
Varietal denomination: 'Snowflame', hardy *Hibiscus.*

FIELD OF THE INVENTION

This plant, as a hybridized hardy *Hibiscus*, is valuable to the landscape market for its improvements in thicker textured and brightly colored flowers and buds, refined "maple-like" foliage with a reddish color, its all-around vigor, compact breaking action, and adaptation to extreme environments, including the ability to consistently survive winter temperatures of at least −30 degrees Fahrenheit.

BACKGROUND OF THE NEW PLANT

The new plant of this invention is the result of a unique hybridization, with the breeding achievement being evidenced in the outstanding combination of characteristics exhibited by this new and distinct *Hibiscus* plant, which include:

(a) Refined, 3-5 lobed 'maple-shaped' leaves with a red-dish-green color and relatively smooth margins which combined compliments the landscape;
(b) Medium-sized flowers that are outstanding for their bright red colored, thick textured and overlapping petals with white color to the reverse side of the petals;
(c) The plant being very floriferous with flowers that stay open for at least one full day, sometimes up to 2 days;
(d) The plant being small to medium-sized but vigorous with compact and uniform breaking action which gives it unique landscape utility; and (e) The plant being so hardy that it can consistently withstand winter temperatures of at least −30 degrees Fahrenheit.

SUMMARY OF THE INVENTION

'Snowflame' was the result of a 50-year breeding program. Its ancestry includes *Hibiscus moscheutos* and *Hibiscus coccineus*. More specifically, the plant resulted from multiple crossings with an unnamed, Fleming-bred *Hibiscus moscheutos* (non patented) and an unnamed Fleming-bred *Hibiscus coccineus* (non patented). The seedling which most nearly met all of the above standards was selected.

This new plant first bloomed in the summer of 2000 and was selected by Gretchen Zwetzig on her property located at 8101 S. 14th St. Lincoln, Nebr. 68516. Asexual propagation of the plant by cuttings and root division in Lincoln, Nebr. has shown that the unique and distinguishing features of the plant are faithfully transmitted from generation to generation and appear to be fixed.

Since its origin, the plant has bloomed from midsummer until frost, while exhibiting the aforementioned distinctive characteristics. This hardy *Hibiscus* plant greatly contributes to the market with its, sheer beauty and utter refinement, its compact growth habit, its enhanced resistance to disease and insects, its stability through extremes in rain and drought, and its extreme hardiness.

BRIEF DESCRIPTION OF THE DRAWINGS

The flower and foliage of the cultivar are shown at 2½ years in the attached photographs.

More specifically, FIG. 1 is a close-up of the flower, leaf and the backside of the flower.

The colors are as true as is reasonably possible to attain in photographic illustrations of this type. The colors illustrated may be slightly off due to light reflectance.

DESCRIPTION OF THE NEW PLANT

What follows is a detailed description of the new cultivar. The specific color descriptions are in accordance with The Royal Horticultural Society Colour Chart (2001), while general color recitations are consistent with ordinary American terminology.

'Snowflame' has not been observed under all possible environmental conditions. It is to be understood that the phenotype may vary significantly with variations in the environment such as temperature, light intensity, humidity, and day length without, however any difference in genotype of the plant. The following botanical characteristics and observations are gathered from the plant when grown in Lincoln, Nebr. (USDA Zone 4).

PLANT

Parentage: Seed Parent: *Hibiscus moscheutos*, unnamed and unpatented Fleming-bred seedling. Pollen Parent: *Hibiscus coccineus*, unnamed and unpatented Fleming-bred seedling.

Comparison between observed plant and parents: Observed Plant is approximately 1 foot shorter than parents and has a 2 inch bigger flower.

Comparison between observed plant and other known cultivars: Observed Plant is unique, but most similar to other patented Fleming hardy *Hibiscus*: Fireball U.S. Plant Pat. No. 13,631, and Torchy U.S. Plant Pat. No. 13,913 and the other patented Fleming hardy *Hibiscus* in that: (a) They are all more compact at apx. 3 feet on average. (b) They are now hardy to −30 degrees Fahrenheit. (c) They all have refined new leaf colors and shapes. (d) They all have thick overlapping, new flowers with new colors that bloom from the top to the bottom of the plant until frost. 'Snowflame' has brighter red flowers than the comparatives.

Origin: A selected seedling from stated cross.

Type of plant: Hardy, herbaceous perennial.

Classification: Variety of hardy *Hibiscus* plant.

Propagation: Relatively easy to propagate by cuttings in approximately 2 weeks; holds its distinguishing characteristics through successive cuttings and divisions.

Size: About 3-3½ feet tall and about 2½ feet wide approximately 30 inches.

Form: Symmetrical annual growth from perennial roots.

Habit: Upright and uniformly branched.

Growth: Vigorous; medium and compact. Full grown (3-3½ ft) in 2 years.

Hardiness: Hardy to at least −30 degrees Fahrenheit.

General health: Plant is very disease resistant against rot, aphids, spider mites, scale, white fly etc.; sturdy through excessive drought, rain or wind.

Foliage:

1. *Arrangement*.—Alternate.
2. *Shape*.—Juvenile: 3-5 lobed "maple-shaped" leaves. Rounded base shape. Mature: Refined, "maple-shaped", 3-5 lobed leaf with entire to mildly serrate margins and acute apices; rounded base.
3. *Size*.—Mature leaf (petiole base to apex): Length is about 4.5 to 5.31 inches or 11½ to 13½ cm, width is about 3½ to 5 inches or 9 to 12½ cm.
4. *Color*.—Young leaves (upper side)146 A: (red cast) 59 A. Mature leaves: (upper side): 148A, (purple cast) 59 A. Veins: 61-A and 59 A. Venation pattern: Palmate. Upper and Lower Venation color: 59 A and 61A. Coloration of the Mature lower leaf surface: Closest to; a little lighter than 146 B. Young: Between 148 B and C.
5. *Surface texture*.—Pubescent. Low sheen. Upper: Smooth. Lower: Semi-smooth.
6. *Petiole length*.—About 2¾ inches or 6.985 cm. Petiole diameter: 2 cm.
7. *Petiole color*.—146 B and 59 A. Surface texture: Semi-smooth.

Stems: The stems are stout at the base, becoming more slender toward the apices; coloration is consistent with the petiole.

*Length*.—2-3 inches on average.
*Diameter*.—2 cm.
*Internode length*.—2 inches on average.
*Stem texture*.—Semi-smooth.
*Stem color*.—147 B and 59A.

Blooming period: Profuse from July until frost.

Flower diameter: Large; about 10½ inches (26.67 cm).

Borne: Singly in the leaf axils, from midpoint of stems upward.

Bloom duration: Individual bloom lasts at least one full day; possibly up to 2 days.

Form: Campanulate; petals are also very overlapping.

Average number of flowers per season: 300.

Bud:

1. *Length*.—About 2¾ inches or (6.98 cm) on day before opening. Diameter: 1-2 inches.
2. *Color*.—Between 52 A.
3. *Surface texture*.—Semi-glabrous.
4. *Duration*.—One week.

Corolla: Having five petals.

1. *Petal character and dimensions*.—Entire width: 10½ inches (26.67 cm). Campanulate and very overlapping and thick textured. (a) Single Petal Length: About 5 inches or 12.7 cm. (b) Flat Petal Width: About 5½ inches or 13.97 cm.
2. *Coloration*.—Bright red with "white" reverse petal color. (a) Red petals: 53 C. Upper. Coloration of reverse petal surface: Between N 155B and 65 C. (b) Venation in petals: Darker than 53 C. (c) Eye zone: Between 46-A and 53-B. (d) Margin: Markings N 66 C.
3. *Texture*.—Soft, Smooth.
4. *Substance*.—Very thick.
5. *Shape*.—Campanulate and very overlapping.

Reproductive organs:

1. *Staminal column*.—Stamen along basal two-thirds. One per flower. Staminal column length: About 2½ inches or (6½ cm). Filament length: 1¼"; Apx. 100 Stamens per flower. Stamen Color Designation: 4 D. Pollen color: 4 D.
2. *Style*.—Terminates upper one-third of staminal column. Average length: 1". Color: 61 C. Stigmatic lobe color: 61-C. Average size: ½".

Calyx: Shape: 5 lobed, connate at the base; about 1¾ inches or (4.44 cm) in length. One per flower. Upper and Lower Color: Between 146-A and 146-B. Surface texture: Semi-smooth.

Stipules: None.

Epicalyx: Whorl of bracts.

1. *Shape.*—10-12 slender, sword-shaped bractlets.
2. *Length.*—About 1.89 inches or (4.8 cm).
3. *Upper and Lower Surface Color:* 143-A.

Penduncle:

1. *Length.*—About 1½ inches or (3.8 cm).
2. *Strength.*—Stiff and sturdy. Surface texture: Semi-smooth.
3. *Color.*—Light to medium green with slight reddish-purple cast. 146-A with 61-C.

Seeds (fruit): Size: 1 cm. Color: Grey-brown. Average number: Less than 100.

The invention claimed is:

1. A new and distinct cultivar of hardy *Hibiscus* plant, as herein shown and described, characterized by its compact nature, refined reddish "maple-like" foliage of a green and red coloration, its large glowing red flowers with a white reverse, its vigor and its hardiness.

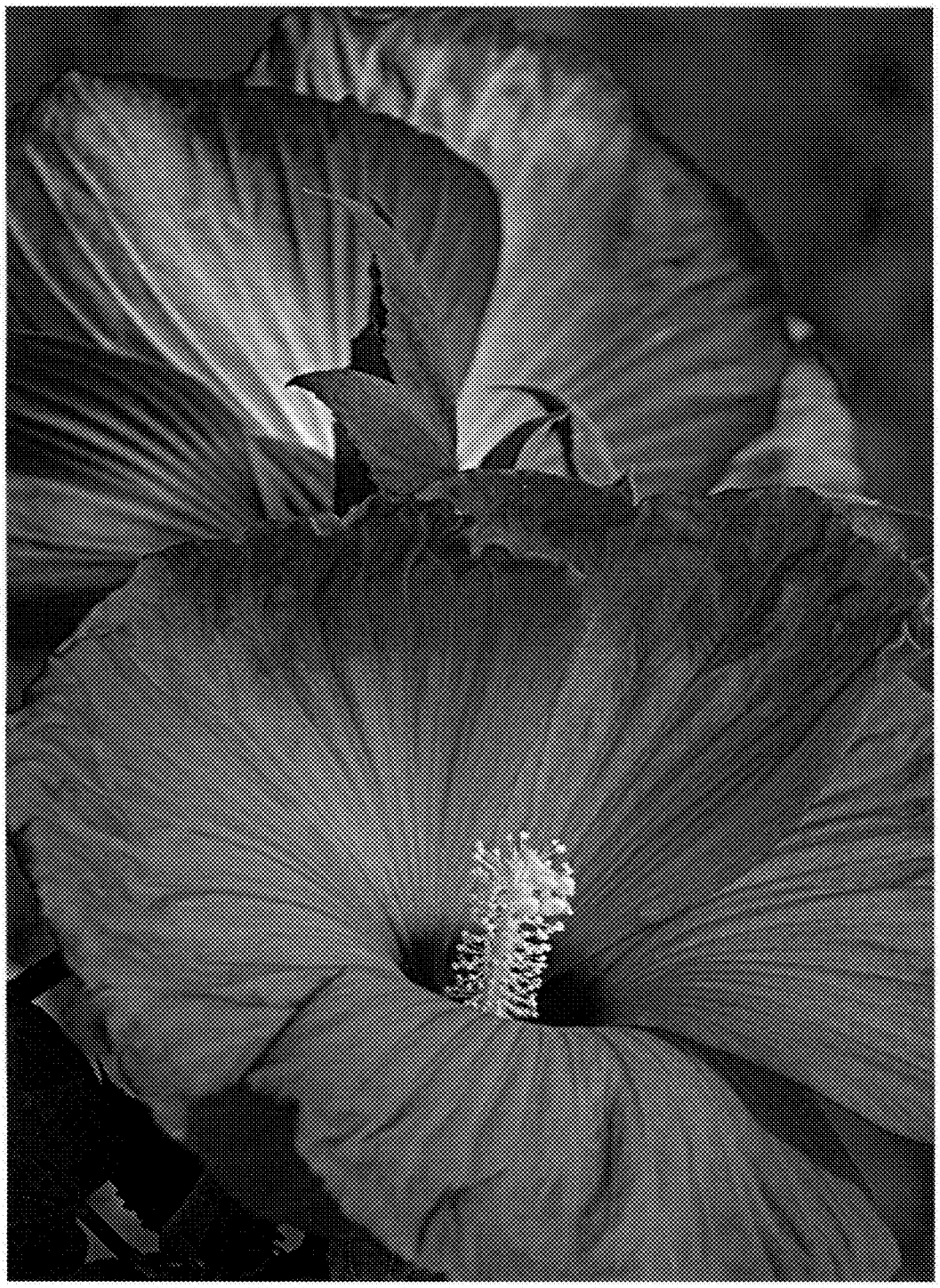

* * * * *